(12) United States Patent
Petitou

(10) Patent No.: US 6,670,338 B1
(45) Date of Patent: Dec. 30, 2003

(54) PENTASACCHARIDES PROCESSES FOR THEIR PREPARATION AND PHARMACEUTICAL COMPOSITIONS CONTAINING THEM

(75) Inventor: Maurice Petitou, Paris cedex (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 09/600,516

(22) PCT Filed: Jan. 13, 1999

(86) PCT No.: PCT/FR99/00045

§ 371 (c)(1),
(2), (4) Date: Jul. 16, 2001

(87) PCT Pub. No.: WO99/36428

PCT Pub. Date: Jul. 22, 1999

(30) Foreign Application Priority Data

Jan. 19, 1998 (FR) .............................................. 98 00514

(51) Int. Cl.$^7$ ...................... C07H 15/04; C08B 37/00; A61K 31/70
(52) U.S. Cl. ...................... 514/54; 514/25; 536/123.1; 536/122
(58) Field of Search .................. 514/54, 25; 536/123.1, 536/122

(56) References Cited

FOREIGN PATENT DOCUMENTS

WO      WO 98/03554      7/1997

OTHER PUBLICATIONS

Sakairi, et al., Chem. Euro. J. 2(8), 1007–1013 (1996); "Synthesis of a Conformationally Constrained Heparin–Like Pentasaccharide".
Ragazzi et al., Carbohydrate Research 195(2), 169–186 (1990); "Conformation Of The Pentasaccharide Corresponding To The Binding Site Of Heparin for Antithrombin III".

Primary Examiner—Samuel Barts
Assistant Examiner—Michael C. Henry
(74) Attorney, Agent, or Firm—Paul E. Dupont; Michael D. Alexander

(57) ABSTRACT

Pentasaccharides in acidic form and their pharmaceutically acceptable salts, the anionic form thereof having the formula:

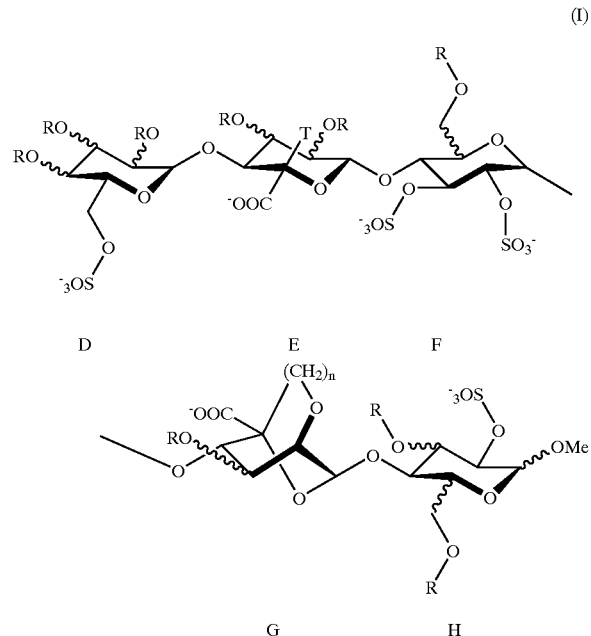

wherein:

R represents hydrogen or an —SO$_3^-$, (C$_1$–C$_3$)alkyl or (C$_2$–C$_3$)acyl group;

T represents hydrogen or an ethyl group; and n represents 1 or 2 for use in the treatment of pathologies associated with a clotting dysfunction.

15 Claims, 7 Drawing Sheets

SCHEME 1 - Preparation of the donor monosaccharide: preparation of the precursor GH (17)

SCHEME 1 – (continued 1): Preparation and first conversions of the disaccharide

SCHEME 1 - (continued 2): Construction of the bicyclic system

SCHEME 2: Condensation of the imidate DEF (18) with GH (17), deprotection and sulphation.

SCHEME 3: Preparation of the donor EF, disaccharide 29

SCHEME 4: Preparation of the acceptor tetrasaccharide 31

SCHEME 5: Coupling of the tetrasaccharide EFGH (31) with the glycosyl donor D (32), deprotection and sulphation.

PENTASACCHARIDES PROCESSES FOR THEIR PREPARATION AND PHARMACEUTICAL COMPOSITIONS CONTAINING THEM

This is the National Phase Application of PCT/FR99/00045, filed Jan. 13, 1999.

The present invention relates to penta-saccharides, to processes for their preparation and to pharmaceutical compositions containing them.

Heparin is a polysaccharide of the glycosamino-glycan family which is known for its anticoagulant properties. It is known (I. Björk and U. Lindahl, Molecular and Cell Biochemistry, 1982, Dr. W. Junk Publishers-Netherlands) that blood clotting is a complex biological phenomenon. Certain stimuli, such as contact activation and tissue factor, trigger the subsequent activation of a series of clotting factors present in blood plasma. Irrespective of the nature of the stimulus, the final steps are identical, the activated factor X (Xa) activates factor II (also known as prothrombin), which, in its activated form (factor IIa, also known as thrombin), gives rise to partial proteolysis of soluble fibrinogen with release of insoluble fibrin, which is one of the main constituents of a blood clot.

Under normal physiological conditions, the activity of the clotting factors is regulated by proteins such as antithrombin III (ATIII) and heparin cofactor II (HC II), which are also present in plasma. AT III exerts inhibitory activity on a certain number of clotting factors, and in particular on factors Xa and IIa.

Inhibition of factor Xa or of factor IIa is thus the preferred means for obtaining anticoagulant and antithrombotic activity, since these two factors are involved in the final two steps of clotting, which are independent of the triggering stimulus.

A pentasaccharide such as the one described by P. Sinay et al., Carbohydrate Research 1984, 132 C5 represents the minimum heparin sequence required for binding to AT III. This compound was obtained about fifteen years ago by total chemical synthesis.

Since then, a certain number of synthetic oligosaccharides, obtained by total chemical synthesis and having antithrombotic anticoagulant activity, have been described in the literature.

Patent EP 0,084,999 describes derivatives consisting of uronic acid (glucuronic or iduronic acid) monosaccharide units and glucosamine which have advantageous antithrombotic properties. Besides substituents consisting of hydroxyl groups, these compounds contain N-sulphate groups, N-acetyl groups and, in certain cases, the anomeric hydroxyl groups are replaced with methoxy groups.

Application EP 0,165,134 also describes synthetic oligosaccharides with antithrombotic activity. These compounds, consisting of uronic acid monosaccharide units and glucosamine and containing an O-sulphate group in position 3 of the glucosamine unit, are also described in application EP 0,301,618. These compounds have powerful antithrombotic and anti-coagulant properties. Patent EP 0,454,220 describes uronic acid derivatives and glucose derivatives which contain O-alkyl or O-sulphate groups as substituents. These latter compounds also have antithrombotic and anticoagulant properties.

Sulphated glycosaminoglycanoid derivatives in which the N-sulphate, N-acetate or hydroxyl functional groups have been replaced with alkoxy, aryloxy, aralkyloxy or O-sulphate groups are also described in patent EP 0,529,175. These compounds have advantageous antithrombotic properties. The latter compounds are also inhibitors of smooth muscle cell proliferation.

Oligosaccharides, and in particular penta-saccharides, which are analogous to the minimum heparin sequence required for binding to AT-III are described in Angew. Chem. Int. Ed. Engl. 1993, 32, 3, 434–436. These compounds contain glucuronic acid or glucose units whose hydroxyl functions have been replaced with O-sulphate or O-methyl groups.

Many studies have since been carried out on pentasaccharides, and it has been indicated in the literature that the conformation of the L-iduronic acid unit G plays an important role in the activity of the products. Several conformational states for the unit G have been described ($^4C_1$, $^1C_4$, $^2S_O$) and it has been suggested that this conformational flexibility is essential for the biological activity of products containing L-iduronic acid (B. Casu, M. Petitou, A. Provasoli and P. Sinay, Conformational flexibility: a new concept for explaining binding and biological properties of iduronic acid-containing glycosamino-glycans. Trends Biochem. Sci. 1988, 13, 221–225).

It has now been found, surprisingly, that by replacing one of the O-alkyl groups with an alkylene bridge, and thus by locking the conformation of the L-iduronic acid, oligosaccharides are obtained which have advantageous biological properties although lacking in conformational flexibility. The reason for this is that the compounds of the present invention differ from the other synthetic heparinoids described in the literature, by virtue of their novel structures and their powerful and unexpected biological properties. The compounds of the invention are pentasaccharides in which the L-iduronic unit G is in the so-called "locked"$^2S_O$ conformation and in which the D-glucuronic acid unit E optionally has an ethyl group in position 5. These compounds have very great anti-factor Xa activity and great affinity for AT III.

The subject of the present invention is, more particularly, a pentasaccharide in acidic, form and its pharmaceutically acceptable salts, with one or more pharmaceutically acceptable cations, the anionic form of which has the formula (I):

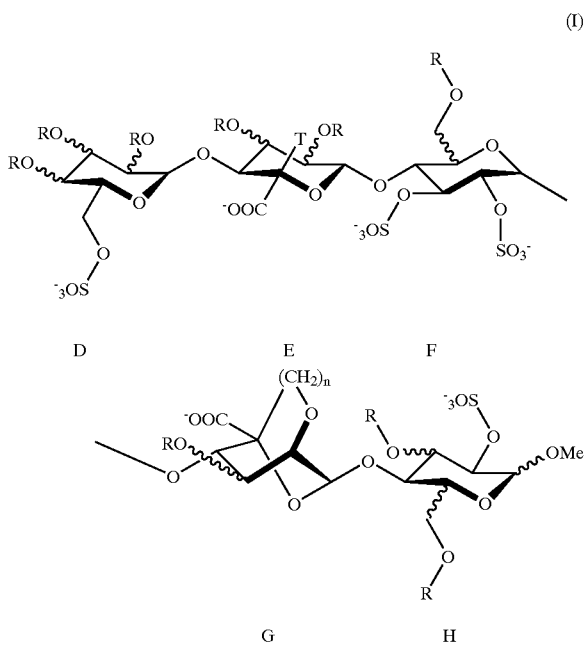

in which:

R represents hydrogen or an —SO$_3^-$, (C$_1$–C$_3$)alkyl or (C$_2$–C$_3$)acyl group;

T represents hydrogen or an ethyl group; and n represents 1 or 2.

The invention encompasses pentasaccharides in acidic form, or in the form of a pharmaceutically acceptable salt. In the acidic form, the —COO and —SO$_3$ functions are in the form —COOH and —SO$_3$H, respectively.

The expression "pharmaceutically acceptable salt of the pentasaccharides of the invention" is intended to refer to pentasaccharides in which one or more of the —COO and/or —SO$_3$ functions are ionically bonded to a pharmaceutically acceptable metal cation.

The preferred salts according to the invention are those in which the cation is chosen from the cations of alkali metals and, even more preferably, those in which the cation is Na$^+$ or K$^+$.

The subject of the present invention is also a process for preparing the pentasaccharides of the invention, characterized in that a precursor of the unit G is prepared, which is coupled with a precursor of the unit H to give a precursor of GH, the pentasaccharide finally being obtained: either by coupling a precursor of GH with a precursor of DEF, or by coupling a precursor of GH with a precursor of EF, followed by addition of D.

Any precursor of G, of H, of EF or of DEF can be used. This means that it is possible, according to s these processes, to prepare an entire family of pentasaccharides having the unit G of locked configuration in common.

The process described above is the preferred process of the invention. However, the pentasaccharides of the invention can be prepared by other known methods of sugar chemistry, and in particular by reacting a monosaccharide containing protective groups such as described by T. W. Green, in Protective Groups in Organic Synthesis (Wiley, N.Y. 1981), on the hydroxyl radicals and optionally on the carboxyl radicals, if present, with another protected monosaccharide, to form a disaccharide which is then reacted with another protected monosaccharide to form a protected trisaccharide, from which a protected tetrasaccharide and then a protected pentasaccharide can be obtained.

The protected pentasaccharides are then deprotected and optionally sulphated, or partially deprotected, then sulphated and then deprotected, in order to obtain the compounds of the invention.

Such processes are known in carbohydrate chemistry, and are described in particular by G. Jaurand et al. in Bioorganic and Medicinal Chemistry Letters 1992, 2, 9, 897–900, by J. Basten et al., in Bioorganic and Medicinal Chemistry Letters 1992, 2, 9, 905–910 and by M. Petitou and C. A. A. van Boeckel in "Chemical synthesis of heparin fragment and analogues" 203–210—Process in the chemistry of organic natural products, Ed. Springer Verlag Vienna—N.Y. 1992.

The process described above makes it possible to obtain the compounds of the invention in the form of salts. In order to obtain the corresponding acids, the compounds of the invention in the form of salts are placed in contact with a cation-exchange resin in acidic form.

The compounds of the invention in the form of acids can then be neutralized with a base in order to obtain a desired salt.

To do this, any inorganic or organic base which gives pharmaceutically acceptable salts can be used.

Sodium hydroxide, potassium hydroxide, calcium hydroxide or magnesium hydroxide is preferably used. The sodium and calcium salts of the pentasaccharides of the invention are the preferred salts.

The compounds which are the subject of the present invention have advantageous pharmacological and biochemical properties. More particularly, they have great anti-factor Xa activity and great affinity for AT III.

As has been mentioned above, in its clotting cascade, factor Xa activates prothrombin into thrombin, which proteolyses soluble fibrinogen with release of insoluble fibrin, the main constituent of a blood clot.

Inhibition of factor Xa is thus a preferred means for obtaining anticoagulant and antithrombotic activity. The anti-factor Xa activity of the products of the invention was evaluated at pH 7, according to the method described by Teien A. N. and Lie M., in Thrombosis Research 1977, 10, 399–410, and it has been demonstrated that the products of the invention have anti-Xa activity equal to or greater than that of the synthetic heparinoids already known.

The affinity of the pentasaccharides of the invention, the anion of which has the formula (I), for AT III was determined by spectrofluorimetry, under the conditions described by D. Atha et al. in Biochemistry 1987, 26, 6454–6461. The results of the tests demonstrated that the compounds of the invention have very great affinity for AT III.

Moreover, the overall antithrombotic activity of these compounds was evaluated in rats by means of a model of venous stasis and induction with thrombo-plastin, according to the method described by J. Reyers et al. in Thrombosis Research 1980, 18, 669–674.

The ED$_{50}$ of the compounds of the invention is at least of the same order as or less than that of the other synthetic heparinoids already known. The compounds of the invention thus have advantageous specificity of action and advantageous anticoagulant and antithrombotic activity.

The compounds of the invention are useful for preparing pharmaceutical compositions for parenteral administration.

The compounds of the invention are of very low toxicity; their toxicity is entirely compatible with their use as medicines.

The compounds of the invention are very stable and are thus particularly suitable to be the active principle of medicines.

The invention also covers pharmaceutical compositions containing, as active principle, a compound according to the invention or one of its pharmaceutically acceptable salts, optionally combined with one or more inert and appropriate excipients.

In each unit dose, the active principle is present in the amounts which are suited to the daily doses envisaged. Each unit dose contains from 0.1 to 100 mg of active principle, preferably from 0.5 to 50 mg.

The compounds according to the invention can also be used in combination with one or more other active principles which are useful for the desired therapy, such as, for example, antithrombotic agents, anticoagulants, anti-platelet-aggregating agents such as, for example, dipyridamole, aspirin, ticlopidine, clopidogrel or antagonists of the IIb/IIIa glycoprotein complex.

The pharmaceutical compositions are formulated for administration to mammals, including man, for the treatment of the abovementioned diseases.

Pharmaceutical compositions thus obtained are advantageously in various forms such as, for example, injectable or drinkable solutions, sugar-coated tablets, plain tablets or gelatin capsules. The injectable solutions are the preferred pharmaceutical forms. The pharmaceutical compositions of the present invention are useful in particular for the preventive or curative treatment of vascular wall disorders, such as atherosclerosis, hypercoagulability states observed, for example, after tumour surgery or disruption of clotting, induced by bacterial, viral or enzymatic activators.

More generally, the pentasaccharides of the invention can be used in the treatment of pathologies associated with a clotting dysfunction.

The dosage can vary within a wide range depending on the patient's age, weight and state of health, the nature and severity of the complaint and the route of administration. This dosage comprises the administration of one or more doses of from about 0.5 mg to about 1000 mg per day, preferably from about 1 to about 100 mg per day and better still from about 0.5 to about 50 mg per day, for example about 20 mg per day, intramuscularly or subcutaneously in batchwise administrations or administrations at regular intervals, or of a daily dose of about 200 mg to about 1000 mg per day orally.

Naturally, these doses can be adjusted for each patient, depending on the results observed and on the blood analyses carried out beforehand.

Subcutaneous administration is the preferred route

The subject of the present invention is thus also pharmaceutical compositions which contain, as active principle, one of the above compounds optionally combined with another active principle. These compositions are made so as to be able to be administered digestively or parenterally.

In the pharmaceutical compositions of the present invention for oral, sublingual, subcutaneous, intramuscular, intravenous, transdermal, transmucous, local or rectal administration, the active ingredient can be administered in unit forms of administration, mixed with standard pharmaceutical supports, to animals and to human beings. The appropriate unit forms of administration comprise oral forms such as oral suspensions, solutions, granules and powders, gelatin capsules and tablets, sublingual and buccal forms of administration, subcutaneous, intramuscular, intravenous, intranasal or intraocular forms of administration and rectal forms of administration.

When a solid composition is prepared in the form of tablets, the main active ingredient is mixed with a pharmaceutical vehicle such as gelatin, starch, lactose, magnesium stearate, talc, gum arabic or the like. The tablets can be coated with sucrose or other suitable materials or alternatively they can be treated such that they have sustained or delayed activity and so that they continuously release a predetermined amount of active principle.

A preparation as gelatin capsules is obtained by mixing the active ingredient with a diluent and pouring the mixture obtained into soft or hard gelatin capsules.

The water-dispersible powders or granules can contain the active ingredient mixed with dispersing agents or wetting agents, or suspending agents, such as polyvinylpyrrolidone, as well as with sweeteners or flavour enhancers.

For rectal administration, use is made of suppositories which are prepared with binders which melt at rectal temperature, for example cocoa butter or polyethylene glycols.

For parenteral, intranasal or intraocular administration, aqueous suspensions, isotonic saline solutions or sterile and injectable solutions which contain pharmacologically compatible dispersing agents and/or wetting agents, for example propylene glycol or butylene glycol, are used.

For transmucous administration, the active principle can be formulated in the presence of a promoter such as a bile salt, a hydrophilic polymer such as, for example, hydroxypropylcellulose, hydroxypropylmethylcellulose, hydroxyethylcellulose, ethylcellulose, carboxymethylcellulose, dextran, polyvinylpyrrolidone, pectins, starches, gelatin, casein, acrylic acids, acrylic esters and copolymers thereof, vinyl polymers or copolymers, vinyl alcohols, alkoxy polymers, polyethylene oxide polymers, polyethers or a mixture thereof.

The active principle can also be formulated in the form of microcapsules, optionally with one or more supports or additives.

The active principle can also be in the form of a complex with a cyclodextrin, for example α-, β- or γ-cyclodextrin, 2-hydroxypropyl-β-cyclodextrin or methyl-β-cyclodextrin.

The active principle can also be released by a balloon containing it or by an endovascular extender introduced into the blood vessels. The pharmacological efficacy of the active principle is thus not affected.

Subcutaneous administration is the preferred route.

The methods, the preparations and the schemes which follow illustrate the synthesis of the various intermediates which are useful for obtaining the pentasaccharides according to the invention.

The following abbreviations are used: TBDMS: tert-butyldimethylsilyl; Lev: levulinyl; Bn: benzyl; Bz: benzoyl; TLC: thin layer chromatography; Olm: trichloroacetimidyl; LSIMS: liquid secondary ion mass spectrometry; ESIMS: electron spray ionization mass spectrometry; TMS: trimethylsilyl; TSP: sodium trimethylsilyltetradeuteropropionate; Tf: triflate; MS: molecular sieves; All: allyl; PMB: p-methoxybenzyl; SE: trimethylsilylethyl. Dowex®, Sephadex®, Chelex® and Toyopearl® are registered trade marks.

In the methods, the preparations and the examples described below, the general procedures relating to the catalytic coupling of the imidates, the cleavage of the levulinic esters, the catalytic coupling of the thioglycosides, the saponification, methylation and selective deprotection of the p-methoxybenzyl group, the deprotection and sulphation of the oligo- and polysaccharides by hydrogenoloysis of the benzyl esters or ethers, the saponification of the esters or the sulphations can be carried out by applying the general methods below to the appropriate intermediates.

BRIEF DESCRIPTION OF THE FIGURES

FIG. 1 shows the initial steps of reaction scheme 1 for the preparation of monosaccharide 6, FIG. 2 is a continuation of reaction scheme 1 showing the conversion of monosaccharide 6 to disaccharide 12.

FIG. 3 is a continuation of reaction scheme 1 showing the conversion of disaccharide 12 to the bicyclic disaccharide GH (compound 17).

Figure 1:
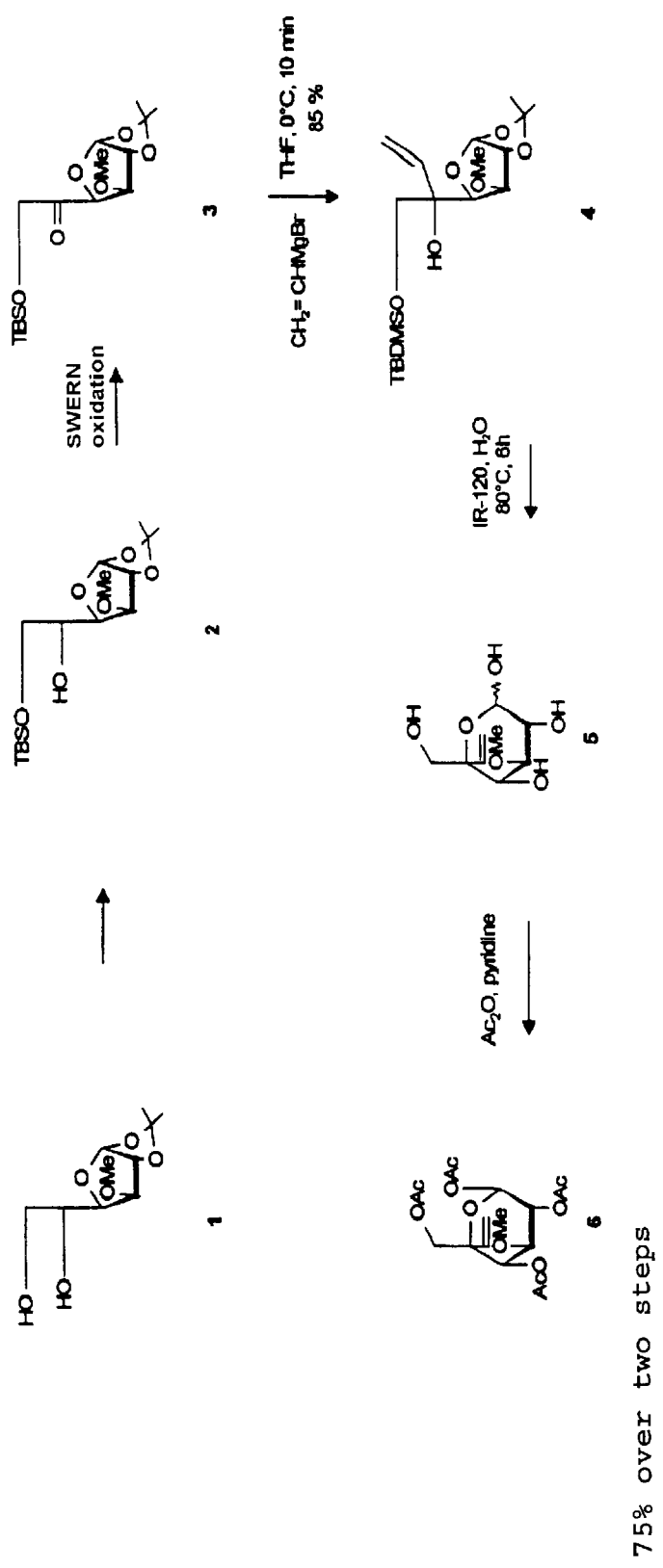
FIGS. 1, 2, and 3 show reaction scheme 1 the the preparation of the precursor disaccharide GH (compound 17).
Figure 2:
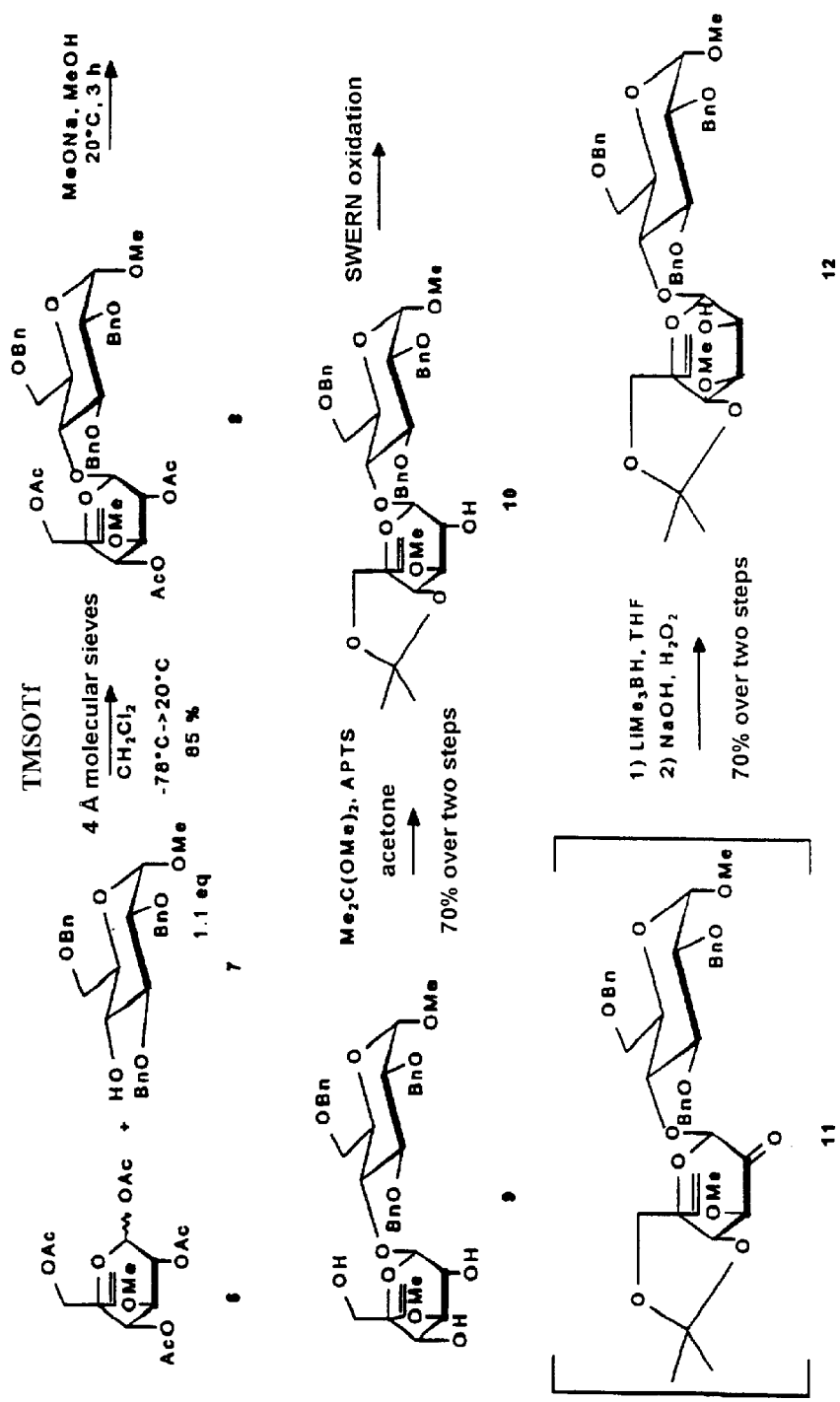
Figure 3:
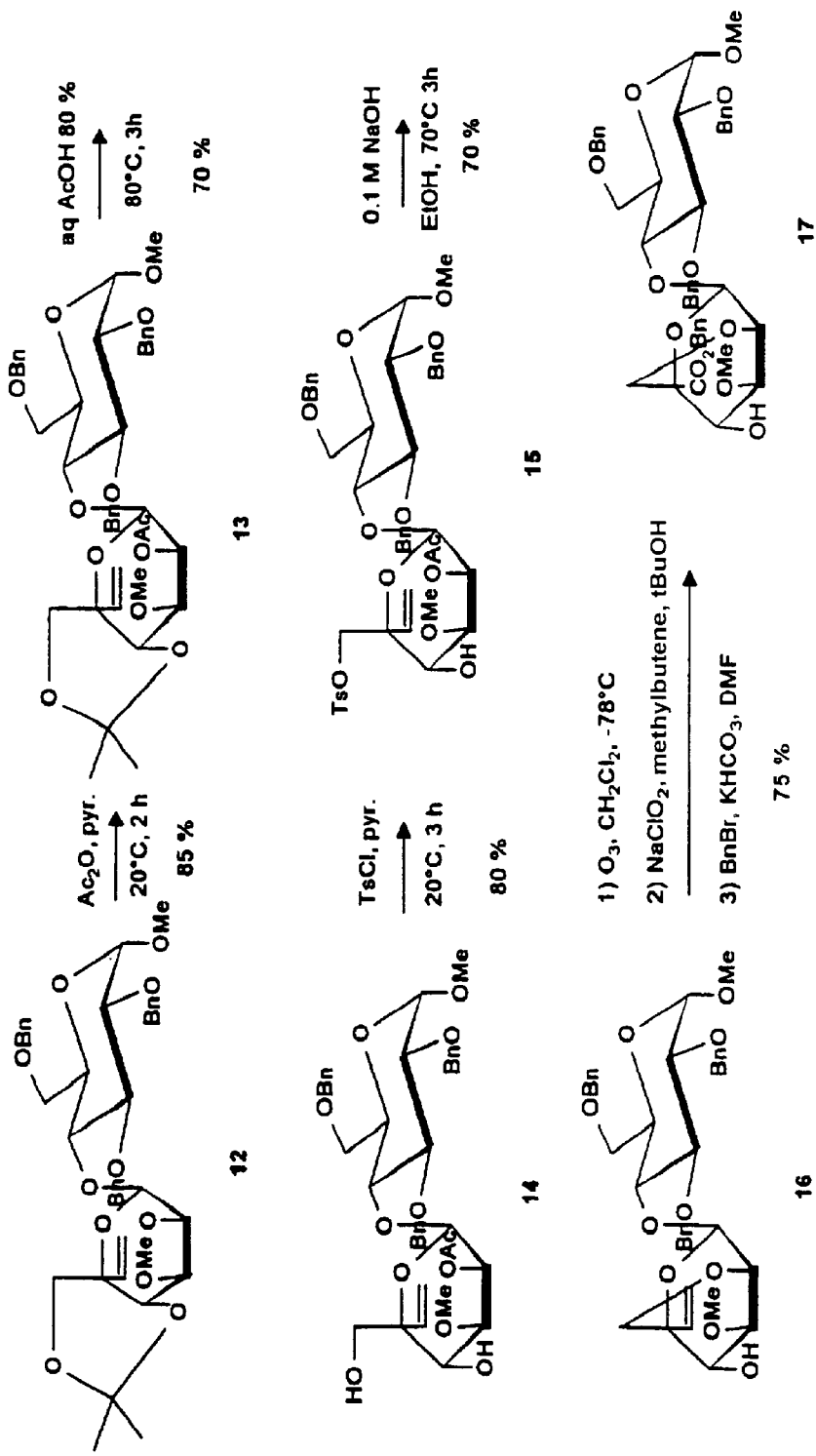
Figure 4:
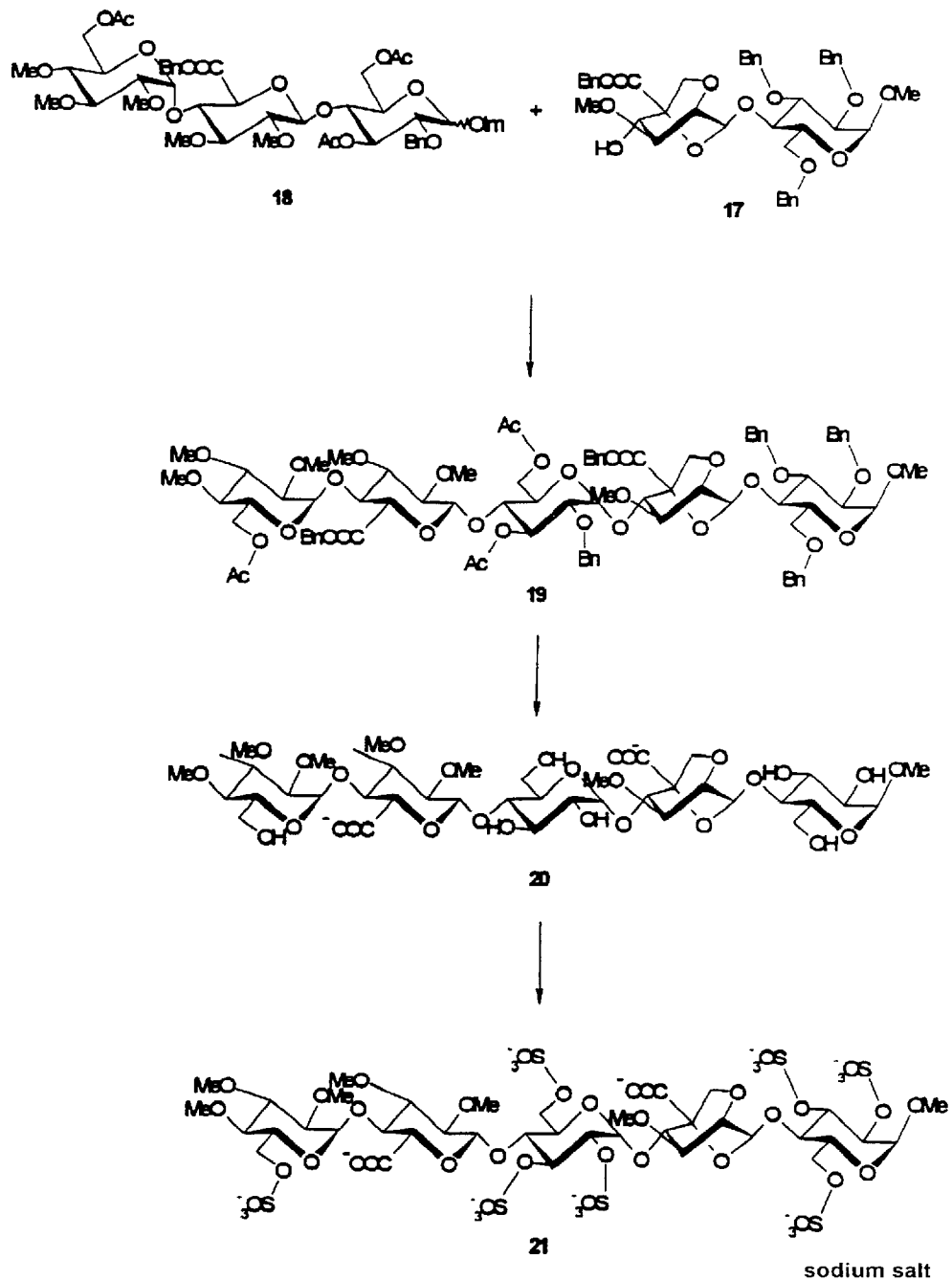
FIG. 4 shows reaction scheme 2 for the coupling of disaccharide GH (compound 17) with trisaccharide DEF (compound 18) to give the pentasaccharide DEFGH (compound 21).
Figure 5:
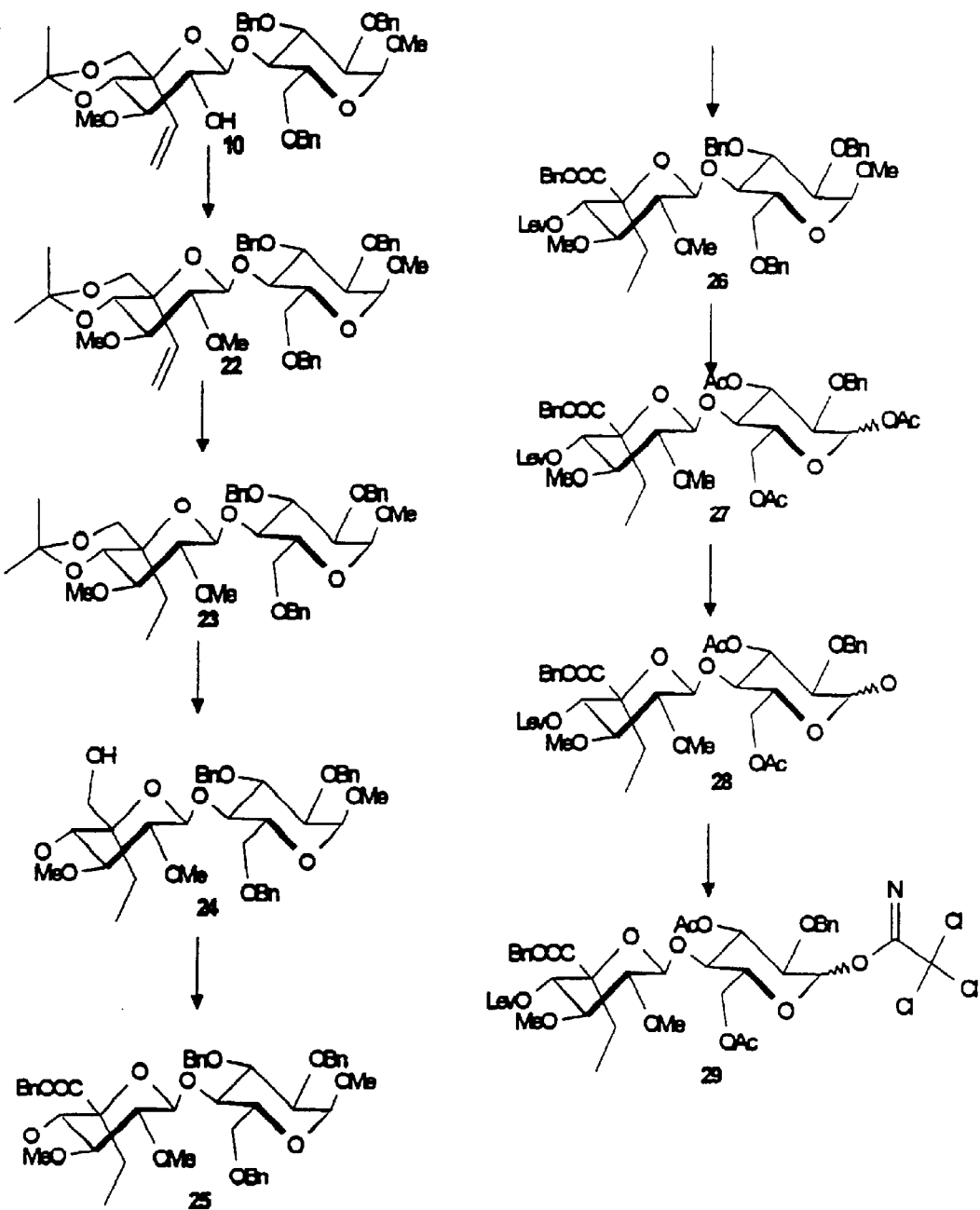
FIG. 5 shows reaction scheme 3 for the preparation of the precursor disaccharide EF (compound 29).
Figure 6:
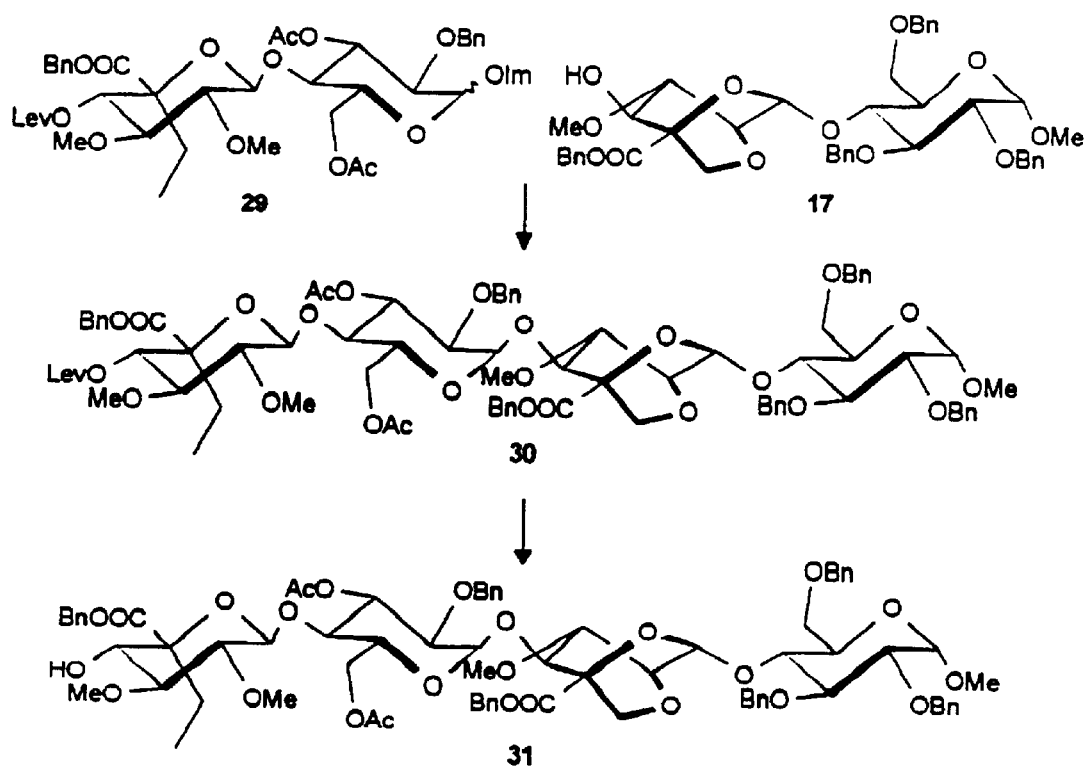
FIG. 6 shows reaction scheme 4 for the coupling of disaccharide EF (compound 29) with disaccharide GH (compound 17) to give the tetrasaccharide EFGH (compound 31).
Figure 7:
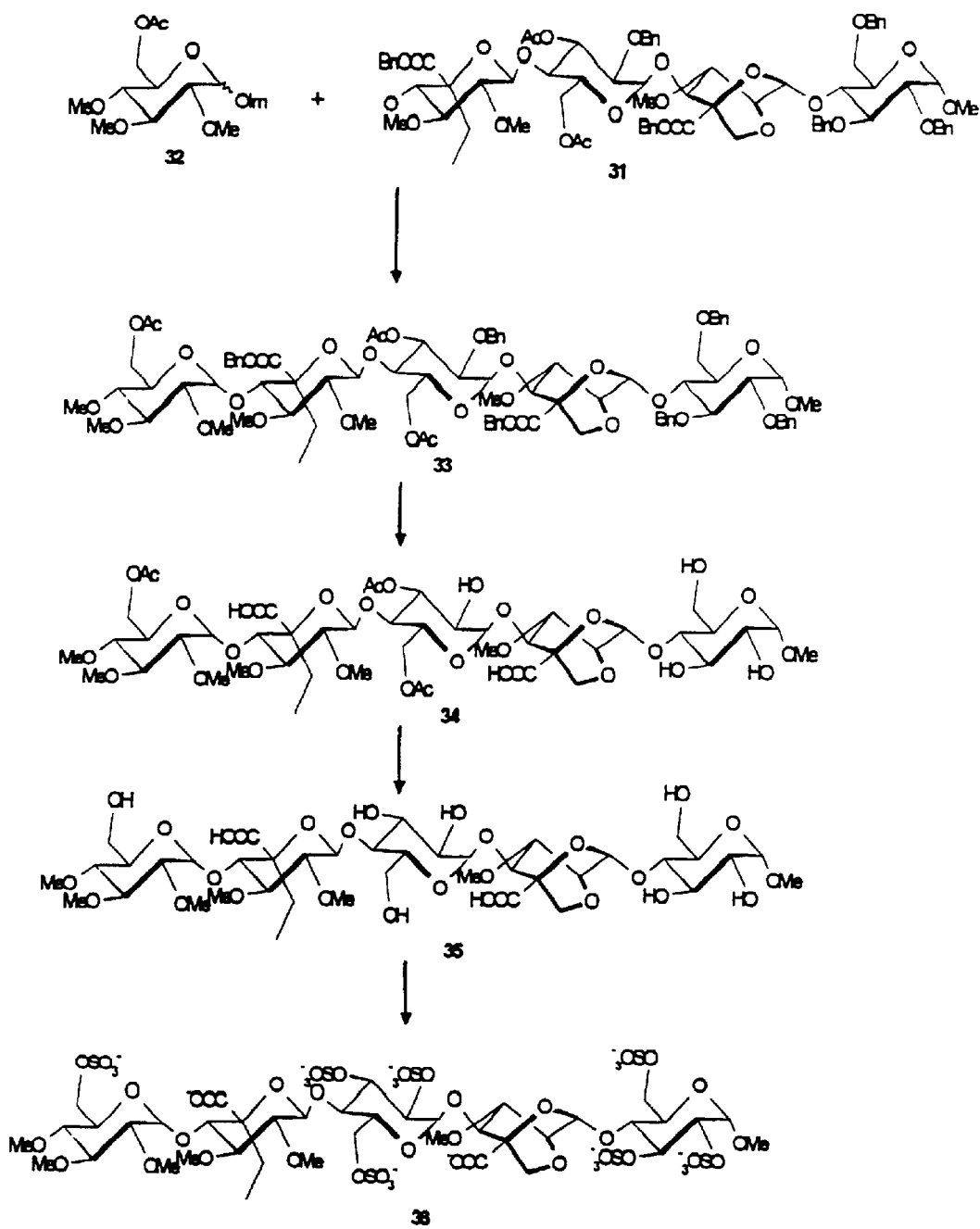
FIG. 7 shows reaction scheme 5 for the coupling of tetrasaccharide EPGH (compound 31) with monosaccharide D (compound 32) to give pentasaccharide DEFGH (compound 36).

The compounds of the present invention are synthesized according to the various preparations described below.

PREPARATION 1

6-O-tert-Butyldimethylsilyl-1,2-O-isopropylidene-3-O-methyl-α-D-glucofuranose (2)

The diol 1 (10 g, 42.7 mmol) is taken up in anhydrous dichloromethane (100 ml) and tert-butyl-dimethylsilyl chloride (7.1 g, 47.3 mmol) and imidazole (5.8 g, 85.3 mmol) are added. The reaction mixture is stirred at room temperature. After 2 hours, the mixture is diluted in dichloromethane and washed with water. The organic phase is dried over magnesium sulphate and concentrated, and the residue is purified by chromatography on a column of silica gel (1/9 v/v ethyl acetate/cyclohexane) to give the desired product 2 (11.9 g, 80%) in the form of a syrup.

$[\alpha]_D$ −34° C. (c 1.9, $CHCl_3$)

PREPARATION 2

6-O-tert-Butyldimethylsilyl-1,2-O-isopropylidene-3-O-methyl-5-C-vinyl-α-D-glucofuranose (4)

Oxalyl chloride (3.2 ml, 36.8 mmol) and dimethyl sulphoxide (5.2 ml, 73.4 mmol) are added, at −78° C., to anhydrous dichloromethane (40 ml) and the mixture is stirred for 30 minutes. Next, compound 2 (6.4 g, 18.4 mmol) is added and the mixture is stirred for a further 1 hour. Next, triethylamine (15.3 ml, 110.0 mmol) is added and, after 30 minutes, the reaction mixture is diluted in dichloromethane. A standard work-up gives the pentulose compound (3), which is used directly for the following reaction. The crude ketone 3 is taken up in anhydrous tetrahydrofuran (100 ml) and a 1 M solution of vinylmagnesium bromide in tetrahydrofuran (28 ml, 27.6 mmol) is added at 0° C. After 1 hour, the reaction mixture is diluted, not with ammonium chloride, and washed with water.

The organic phase is dried over magnesium sulphate and concentrated, and the residue is purified by chromatography on a column of silica gel (1/9 v/v ethyl acetate/cyclohexane) to give the desired compound 4 (70%, 4.8 g) in the form of a syrup.

$[\alpha]_D$ −40° C. (c 1.3, $CHCl_3$). Anal. calculated: C, 57.72, H, 9.15. Found: C, 57.77, H, 9.23.

PREPARATION 3

1,2,4,6-Tetra-O-acetyl-3-O-methyl-5-C-vinyl-β-D-gluco-pyranose (6)

Compound 4 (3.5 g, 9.4 mmol) is taken up in water (50 ml); IR-120 resin (1 g) is added thereto and the mixture is heated at 80° C. for 6 hours. The resin is filtered off and the filtrate is concentrated. The crude product 5 is acetylated using acetic anhydride (12 ml) and pyridine (13 ml). The excess acetic anhydride is destroyed with methanol and the solvents are concentrated. The residue is extracted with water and dichloromethane. The organic phase is dried over magnesium sulphate, concentrated and, after purification by chromatography on a column of silica gel (3/2 v/v ethyl acetate/cyclohexane), the tetraacetate 6 is obtained in the form of a solid (75%, 2.7 g). m.p.=50° C.

$[\alpha]_D$ −84° C. (c 1.6, $CHCl_3$) Anal. calculated: C, 52.47, H, 6.19. Found: C, 52.51, H, 6.19. CI-MS: 406(M+$NH_4$),389 (M+1).

PREPARATION 4

Methyl 2,3,6-tri-O-Benzyl-4-O-(2,4,6-tri-O-acetyl-3-O-methyl-5-C-vinyl-β-D-glucopyranosyl)-α-D-glucano-side (8)

Compound 6 (1.6 g, 4.1 mmol) and compound 7 (2.1 9, 4.5 mmol) (P. J. Garegg and H. Hultberg, Carbohydr. Res. 1981, 93, C10) are dissolved in anhydrous dichloromethane (50 ml) and molecular sieves (4.0 g) are added. The reaction mixture is stirred at room temperature for one hour and TMSOTf (0.95 ml, 5.2 mmol) is then added at −78° C. The reaction mixture is then left to warm gently to room temperature. After 2 hours, the reaction mixture is neutralized with triethylamine and filtered through Celite; the filtrate is washed with water. The organic phase is dried over magnesium sulphate and concentrated, and the residue is purified by chromatography on silica gel (4/1 v/v ethyl acetate/cyclohexane) to give the desired compound 8 (2.77 g, 85%) in the form of a solid. m.p.=47° C.

$[\alpha]_D$ −36° C. (c 0.6, $CHCl_3$) Anal. calculated: C, 65.14, H, 6.61. Found: C, 65.09, H, 6.70.

PREPARATION 5

Methyl 2,3,6-O-tri-O-Benzyl-4-O-(4,6-O-isopropylidene-3-O-methyl-5-C-vinyl-β-D-glucopyranosyl)-α-D-gluco-pyranoside (10)

Compound 8 (2.7 g, 3.4 mmol) is dissolved in methanol (40 ml). Sodium (catalytic) is added at 0° C. and the mixture is stirred at room temperature for 3 hours. The solvent is concentrated and the residue 9 is taken up in anhydrous acetone (40 ml) and 2,2-dimethoxypropane (2 ml) and p-toluenesulphonic acid (catalytic) are added. The reaction mixture is stirred at room temperature overnight. The solvent is evaporated off and the residue is taken up in chloroform and washed with water. The organic phase is dried over magnesium sulphate and concentrated and the residue is purified by chromatography on a column of silica (1/1 v/v ethyl acetate/cyclohexane) to give the 4',6'-isopropylidene-O-derivative 10 (1.7 g, 70%) in the form of a solid. m.p.=55° C.

$[\alpha]_D$ −13° C. (c 0.8, $CHCl_3$). Anal. calculated: C, 67.97, H, 7.13. Found: C, 67.87, H, 7.16. CI-MS: 707(M+1),724 (M+$NH_4$)

PREPARATION 6

Methyl 2,3,6-tri-O-Benzyl-4-O-(4,6-O-isopropylidene-3-O-methyl-5-C-vinyl-β-D-mannopyranosyl)-α-D-gluco-pyranoside (12)

Oxalyl chloride (0.35 ml, 4.0 mmol) and anhydrous DMSO (0.57 ml, 8.0 mmol) are stirred in anhydrous dichloromethane (10 ml) at −78° C. for 30 minutes. Compound 10 (1.4 g, 2.0 mmol) in anhydrous dichloromethane (10 ml) is added to the solution and stirring is continued for a further 45 minutes. The reaction mixture is neutralized by addition of anhydrous triethylamine (1.7 ml, 12.0 mmol) and then diluted with dichloromethane. After washing with water, the organic phase is dried over magnesium sulphate and concentrated, and the residue 11 is used directly for the following reaction without purification. The ketone 11 is taken up in anhydrous tetrahydrofuran (15 ml) and a 1N solution of super hydride in tetrahydrofuran (4 ml, 4.0 mmol) is added at −78° C. The reaction mixture is stirred at room temperature for 1 hour and 5% sodium hydroxide (2 ml) and hydrogen peroxide (1 ml) are then added. The solvent is evaporated off and the residue is taken up in ethyl acetate and washed with water. The organic phase is dried over magnesium sulphate and concentrated, and the residue is purified by chromatography (2/1 v/v ethyl acetate/cyclohexane) to give compound 12 (1.0 g, 70%).

$[\alpha]_D$ −11° C. (c 0.5, $CHCl_3$). CI-MS: 724(M+18), 707 (M+1).

PREPARATION 7

Methyl 2,3,6-tri-O-Benzyl-4-O-(2-O-acetyl-3-O-methyl-5-C-vinyl-β-D-mannopyranosyl)-α-D-glucopyranoside (14)

Compound 12 (940 mg, 1.3 mmol) is dissolved in pyridine (3 ml) and acetic anhydride (0.3 ml) is added. The reaction mixture is stirred at room temperature for 3 hours. The excess pyridine and acetic anhydride is concentrated and the residue 13 is used directly for the deprotection of the isopropylidene, using 80% acetic acid (5 ml) at 60° C. for 2 hours. The excess acetic acid is evaporated off and the residue is purified by chromatography on a column of silica gel (4/1 v/v ethyl acetate/cyclohexane) to give the diol 14 (660 mg, 70%) in the form of a solid. m.p.=53° C.

$[\alpha]_D$ −10° C. (c 0.8, $CHCl_3$). CI-MS: 709(M+1), 726(M+18).

PREPARATION 8

Methyl 2,3,6-tri-O-Benzyl-4-O-(2-O-acetyl-3-O-methyl-6-O-tosyl-5-C-vinyl-β-D-mannopyranosyl)-α-D-gluco-pyranose (15)

Compound 14 (600 mg, 0.9 mmol) is dissolved in pyridine (3 ml) and tosyl chloride (240 mg, 1.3 mmol) is added. The reaction mixture is stirred at room temperature for 3 hours. The solvent is evaporated off and the residue is diluted with chloroform and washed with water. The organic phase is dried over magnesium sulphate and concentrated, and the residue is purified by chromatography on a column of silica gel (1/1 v/v ethyl acetate/cyclohexane) to give the tosyl compound 15 (297 mg, 80%) in the form of a syrup.

$[\alpha]_D$ −26° C. (c 0.8, $CHCl_3$).

PREPARATION 9

Methyl 2,3,6-tri-O-Benzyl-4-O-(2,6-anhydro-3-O-methyl-5-C-vinyl-β-D-mannopyranosyl)-α-D-glucopyranoside (16)

Compound 15 (550 mg, 0.6 mmol) is taken up in ethanol (3 ml) and 0.1N ethanolic sodium hydroxide solution (5 ml) is then added. The reaction mixture is heated at 70° C. for 3 hours and is then neutralized with an IR-120 resin ($H^+$ form) and filtered through Celite. After concentration, the residue is purified by chromatography on a column of silica gel (1/1 v/v ethyl acetate/cyclohexane) to give compound 16 (292 mg, 70%) in the form of a syrup.

$[\alpha]_D$ +13° C. (c 0.5, $CHCl_3$) CI-MS: 666 (M+18).

PREPARATION 10

Methyl 2,3,6-tri-O-Benzyl-4-O-(benzyl-3-O-methyl-2-O-5-C-methylidene-α-L-idopyranuronate)-α-D-gluco-pyranoside (17)

Compound 16 (260 mg, 0.4 mmol) is dissolved in dichloromethane (20 ml), the solution is stirred at −78° C. and ozone is then bubbled through for 30 seconds. The solution turns a pale yellow colour. Dimethyl sulphide is added to the solution and the reaction mixture is then washed with water. The organic phase is dried over magnesium sulphate and concentrated and the following reaction is carried out directly without further purification. The crude aldehyde is taken up in tert-butanol (16 ml) and 2-methyl-2-butene (5 ml) and the water (16 ml) are added. $NaH_2PO_4$ (700 mg) and $NaClO_2$ (700 mg) are then added successively to the mixture. The suspension is stirred vigorously at room temperature overnight, diluted with water and extracted with ethyl acetate. The organic phase is dried over magnesium sulphate and concentrated and the following reaction is then carried out directly. The crude acid is taken up in dimethylformamide (25 ml) and tetrabutylammonium iodide (0.7 g, 2.0 mmol), potassium bicarbonate (0.25 g, 2.5 mmol) and benzyl bromide (0.250 ml, 2.1 mmol) are added. The reaction mixture is stirred at room temperature for 5 hours. The reaction mixture is extracted with water and diethyl ether. The ether phase is dried over magnesium sulphate and concentrated, and the residue is purified by chromatography on a column of silica gel (2/1 v/v ethyl acetate/cyclohexane) to give the derivative 17 (236 mg, 80%) in the form of a syrup. CI-MS: 774 (M+18).

PREPARATION 11

Methyl O-(6-O-Acetyl-2,3,4-tri-O-methyl-α-D-gluco-pyranosyl)-(1→4)-O-(benzyl 2,3-di-O-methyl-α-D-gluco-pyranosyluronate)-(1→4)-O-(3,6-di-O-acetyl-2-O-benzyl-α-D-glucopyranosyl)-(1→4)-(2,6-anhydro-5-C-benzyloxy-carbonyl-3-O-methyl-β-D-mannopyranosyl)-(1→4)-2,3,6-tri-O-benzyl-α-D-glucopyranoside (19).

The imidate 18 (Van der Heijden et al., abstr. 9th Eur. Carbohydr. Symp. Utrecht, July 6–11, 1997; A74, p 154) (81 mg, 78.2 μmol), the acceptor 17 (65 mg, 86.0 μmol) and fine molecular sieves (70 mg, 4 Å) are stirred in a 1/2 (v/v) dichloromethane/diethyl ether mixture (2.4 ml) under an inert atmosphere.

The reaction mixture is stirred for 30 minutes and $NaHCO_3$ is then added to the point of neutralization. After filtration and concentration, the residue is purified on a column of Sephadex® LH 20 gel (1/1 v/v dichloromethane/ethanol) and then on a column of silica gel (1/1 (v/v) ethyl acetate/cyclohexane) to give compound 19 (86 mg, 67%).

$[\alpha]_D$ +66° C. (c 1.0, $CH_2CH_2$) $^1H$ NMR given in Table 1 below.

PREPARATION 12

Methyl O-(2,3,4-tri-O-Methyl-α-D-glucopyranosyl)-(1→4)-O-(2,3-di-O-methyl-β-D-glucopyranosyluronic acid)-(1→4)-O-(α-D-glucopyranosyl)-(1→4)-O-(2,6-anhydro-5-C-carboxy-3-O-methyl-β-D-mannopyranosyl)-(1→4)-α-D-glucopyranoside (20).

According to M. Petitou and C. A. A. van Boeckel, Progress in the Chemistry of Organic Natural Products, published by W. Herz et al. Vienna, Springer-Verlag, New York, 1992, 143–210.

A solution of compound 19 (49 mg, 30.0 μmol) in acetic acid (3 ml) is stirred under hydrogen (3.5 MPa) for 12 hours at 40° C. in the presence of 5% palladium on charcoal (73 mg, 35 b). The mixture is filtered through Celite, concentrated and co-distilled with water (4×5 ml). The residue is dissolved in aqueous 1M NaOH solution (3 ml) and heated at 55° C. for 3 hours. The solution is cooled and passed through a Sephadex® 625 F. column (170 ml) eluted with water. The fractions containing compound 20 are passed through a column of Dowex $H^+$resin. The eluate is concentrated to give compound 20 (25 mg, 86%).

$[\alpha]_D$ +105° C. (c 1.0, $H_2O$) $^1H$ NMR given in Table 1 below.

TABLE 1

| Compound | Unit | H-1 | H-2 | H-3 | H-4 | H-5 | H-6 | H-6' | $J_{1-2}$ (Hz) |
|---|---|---|---|---|---|---|---|---|---|
| 19 ($CDCl_3$) | D | 5.50 | 3.11 | 3.37 | 3.03 | 3.43 | 4.28 | 4.22 | 3.7 |
|  | E | 4.14 | 2.93 | 3.31 | 3.92 | 3.83 | — | — | ~9 |
|  | F | 4.98 | 3.45 | 5.41 | 3.63 | 3.94 | 4.58 | 4.19 | 3.6 |
|  | G | 5.18 | 3.83 | 3.12 | 4.12 | — | 4.10 | 3.98 | ~1 |
|  | H | 4.58 | 3.51 | 4.01 | 3.78 | 3.80 | 3.83 | 3.61 | 3.6 |
| 20 ($D_2O$) | D | 5.50 | 3.33 | 3.49 | 3.30 | 3.50 | 3.74 | 3.74 | 3.9 |
|  | E | 4.62 | 3.26 | 3.58 | 3.90 | 4.04 | — | — | 7.9 |
|  | F | 5.13 | 3.58 | 3.76 | 3.61 | 3.70 to 3.90 | | | 4.1 |
|  | G | 5.23 | 4.35 | 3.71 | 4.20 | — | 4.25 | 4.10 | ~1 |
|  | H | 4.82 | 3.64 | 3.84 | 3.73 | 3.70 to 3.90 | | | 3.7 |

PREPARATION 13

Methyl O-(4,6-O-Isopropylidene-2,3-di-O-methyl-5-C-vinyl-β-D-glucopyranosyl)-(1→4)-2,3,6-tri-O-benzyl-α-D-glucopyranoside (22).

Sodium hydride (0.31 g, 13.0 mmol) is added, at 0° C., to a solution of methyl O-(4,6-O-isopropylidene-3-O-methyl-5-C-vinyl-β-D-glucopyranosyl)-(1→4)-2,3,6-tri-O-benzyl-α-D-glucopyranoside (10) (6.11 g, 8.65 mmol) and methyl iodide (0.80 ml, 13.0 mmol) in N,N-dimethylformamide (9.00 ml). The mixture is left stirring for 2 hours (TLC), methanol is added and the reaction mixture is poured into water. This mixture is extracted with ethyl acetate and the extracts are washed with water, dried and concentrated. The residue is purified on a column of silica (3/2 (v/v) cyclohexane/diethyl ether) to give 22 (5.92 g, 88%). TLC: $R_f$=0.28,(3.2(v/v) cyclohexane/diethyl ether).

PREPARATION 14

Methyl O-(4,6-O-Isopropylidene-2,3-di-O-methyl-5-C-ethyl-β-D-glucopyranosyl)-(1→4)-2,3,6-tri-O-benzyl-α-D-glucopyranoside (23).

Platinum oxide (160 mg) is added to a solution of 22 (5.80 g, 8.04 mmol) in ethyl acetate (400 ml). Hydrogen is introduced. The mixture is left stirring for 40 minutes (TLC), filtered and evaporated to give 23. TLC: $R_f$=0.60 (4/1 (v/v) toluene/ethyl acetate).

PREPARATION 15

Methyl O-(2,3-di-O-Methyl-5-C-ethyl-β-D-glucopyranosyl)-(1→4)-2,3,6-tri-O-benzyl-α-D-glucopyranoside (24).

Crude compound 23 is dissolved in 70% acetic acid (60 ml) and stirred at 80° C. for 2 hours. The mixture is concentrated under vacuum and co-evaporated with toluene to give 24. TLC: $R_f$=0.52 (4/1 (v/v) dichloromethane/methanol).

PREPARATION 16

Methyl O-(Benzyl 2,3-di-O-Methyl-5-C-ethyl-β-D-glucopyranosyluronate)-(1→4)-2,3,6-tri-O-benzyl-α-D-glucopyranoside (25).

2,2,6,6-Tetramethyl-1-piperidyloxy (17.5 mg), sodium hydrogen carbonate solution (17.5 ml), potassium bromide (87 mg) and tetrabutylammonium chloride (115.5 mg) are added to a solution of compound 24 (5.75 g) in tetrahydrofuran (28 ml). The mixture is cooled to 0° C. and a mixture of saturated sodium chloride solution (17 ml), saturated sodium hydrogen carbonate solution (8.70 ml) and sodium hypochlorite (1.3 M, 20 ml) is added over 15 minutes. After stirring for 1 hour, the mixture is diluted with water and extracted (3 times) with dichloromethane. The organic phase is washed with aqueous sodium chloride solution, dried over magnesium sulphate, filtered and evaporated to dryness to give the crude acid derivative.

The acid derivative is dissolved in N,N-dimethylformamide (107 ml) under a nitrogen atmosphere. Potassium hydrogen carbonate (4.10 g) and benzyl bromide (9.70 ml) are added and the mixture is stirred for 16 hours. Ethyl acetate and water are added and, after extraction, the organic phase is concentrated. Purification by chromatography on a column of silica gel gives 3.81 g of compound 25 (60% yield from compound 23).

$[\alpha]_D$ +24 (c=0.15, dichloromethane).

PREPARATION 17

Methyl O-(Benzyl-5-C-ethyl-4-O-levulinyl-2,3-di-O-methyl-β-D-glucopyranosyluronate)-(1→4)-2,3,6-tri-O-benzyl-α-D-glucopyranoside (26).

Compound 25 (3.51 g, 4.46 mmol) is dissolved in anhydrous dioxane (45 ml). Levulinic acid (1.00 g, 8.93 mmol), 1-(3-dimethylaminopropyl)-3-ethylcarbodiimide hydrochloride (1.70 g, 8.93 mmol) and 4-dimethylaminopyridine (0.11 g, 8.93 mmol) are added. The mixture is left stirring for 16 hours and extracted with ethyl acetate, the extracts are washed successively with aqueous 5% potassium hydrogen sulphate solution, with water, with saturated aqueous sodium hydrogen carbonate solution and with water, dried and concentrated. The residue is purified on a column of silica (2/1 and then 3/2 (v/v) cyclohexane/ethyl acetate) to give pure 26 (3.64 g, 85%).

$[\alpha]_D$ +26 (c=0.9, dichloromethane).

PREPARATION 18

O-(Benzyl 5-C-Ethyl-4-O-levulinyl-2,3-di-O-methyl-β-D-glucopyranosyluronate)-(1→4)-1,3,6-tri-O-acetyl-2-O-benzyl-D-glucopyranose (27).

Compound 26 (3.35 g, 3.78 mmol) is dissolved in acetic anhydride (22 ml). The solution is cooled to −20° C. and 22 ml of a cold solution of sulphuric acid in acetic anhydride (1 ml of sulphuric acid in 10 ml of acetic anhydride) is added.

The mixture is diluted with ethyl acetate, washed with saturated aqueous sodium hydrogen carbonate solution, with water, dried and concentrated. The residue is purified on a column of silica (1/1 (v/v) cyclohexane/ethyl acetate) to give 27 (2.20 g, 65.5%). TLC: $R_f$=0.24, (1/1 (v/v) cyclohexane/ethyl acetate)

PREPARATION 19

O-(Benzyl 5-C-Ethyl-4-O-levulinyl-2,3-di-O-methyl-β-D-glucopyranosyluronate)-(1→4)-3,6-di-O-acetyl-2-O-benzyl-D-glucopyranose (28).

Benzylamine (11 ml, 101.4 mmol) is added to a solution of compound 27 (2.18 g, 2.67 mmol) in tetra-hydrofuran (50 ml). The mixture is left stirring for 4 hours. It is extracted with ethyl acetate and the extracts are washed with aqueous 1M hydrochloric acid solution (102 ml) and with water, dried and concentrated. The residue is purified on a column of silica (1/1 (v/v) toluene/ethyl acetate) to give a mixture (α/β=50/50) of compound 28 (1.33 g, 65%).

TLC: $R_f$=0.22 (1/1 (v/v) toluene/ethyl acetate)

PREPARATION 20

O-(Benzyl 5-C-Ethyl-4-O-levulinyl-2,3-di-O-methyl-β-D-glucopyranosyluronate)-(1→4)-3,6-di-O-acetyl-2-O-benzyl-D-glucopyranosyl Trichloroacetimidate (29).

Compound 28 (1.32 g, 1.71 mmol) is dissolved in dichloromethane (34 ml) and trichloroacetonitrile (0.87 ml, 8.50 mmol) and caesium carbonate (0.90 g, 2.73 mmol) are added 15) of imidates 29 (1.20 g, 77%). TLC: $R_f$=0.36 (1/2 (v/v) cyclohexane/ethyl acetate).

PREPARATION 21

Methyl O-(Benzyl 5-C-Ethyl-4-O-levulinyl-2,3-di-O-methyl-β-D-glucopyranosyluronate)-(1→4)-O-(3,6-di-O-acetyl-2-O-benzyl-α-D-glucopyranosyl)-(1→4)-O-(2,6-anhydro-5-C-benzyloxycarbonyl-3-O-methyl-β-D-mannopyranosyl)-(1→4)-2,3,6-tri-O-benzyl-α-D-gluco-pyranoside (30).

A solution of tert-butyldimethylsilyl triflate in dichloromethane (1M, 0.19 ml) is added, under argon at −20° C., to a solution of the imidate 29 (1.19 g, 1.29 mmol) and methyl 2,3,6-tri-O-benzyl-4-(benzyl 3-O-methyl-2-O-5-C-methylidene-α-L-idopyranuronate)-α-D-glucopyranoside 17 (1.02 g, 1.35 mmol) in toluene (40 ml) in the presence of 4 Å molecular sieves (1.93 g). After 30 minutes (TLC), tert-butyldimethylsilyl triflate solution in dichloromethane (1M, 0.19 ml) is again added. After 30 minutes (TLC), solid sodium hydrogen carbonate is added. The solution is filtered, washed with water, dried and evaporated to dryness. The residue is purified by column chromatography on Sephadex® LH20 and then on a column of silica (2/1 (v/v) toluene/ethyl acetate) to give the pure tetrasaccharide 30-α (1.14 g, 58%).

$[α]_D$+47 (c=0.21, dichloromethane)

PREPARATION 22

Methyl O-(Benzyl 5-C-Ethyl-2,3-di-O-methyl-β-D-glucopyranosyluronate)-(1→4)-O-(3,6-di-O-acetyl-2-O-benzyl-α-D-glucopyranosyl)-(1→4)-O-(2,6-anhydro-5-C-benzyloxycarbonyl-3-O-methyl-β-D-mannopyranosyl)-(1→4)-2,3,6-tri-O-benzyl-α-D-glucopyranoside (31).

Compound 30 (1.13 g, 0.75 mmol) is dissolved in a 2/1 (v/v) ethanol/toluene mixture (150 ml) and hydrazine acetate (0.35 g, 3.73 mmol) is added. The mixture is left stirring for 1 hour (TLC) and is concentrated. The residue is purified on a column of silica (3/2 (v/v) toluene/ethyl acetate) to give 31 (0.816 g, 83%).

$[α]_D$+35 (c=1.01, dichloromethane).

PREPARATION 23

Methyl O-(6-O-Acetyl-2,3,4-tri-O-methyl-α-D-glucopyranosyl)-(1→4)-O-(benzyl 5-C-ethyl-2,3-di-O-methyl-β-D-glucopyranosyluronate)-(1→4)-O-(3,6-di-O-acetyl-2-O-benzyl-α-D-glucopyranosyl)-(1→4)-O-(2,6-anhydro-5-C-benzyloxycarbonyl-3-O-methyl-β-D-mannopyranosyl)-(1→4)-2,3,6-tri-O-benzyl-α-D-glucopyranoside (33).

6-O-Acetyl-2,3,4-tri-O-methyl-D-glucopyranose trichloroacetimidate 32 (34.7 mg, 0.0245 mmol) (P. Westerduin, et al. BioOrg. Med. Chem., 1994, 2, 1267) and the glycosyl acceptor 31 (80 mg, 0.056 mmol) are treated according to Preparation 21. The compound is purified on a Sephadex® LH-20 chromatography column (1/1 (v/v) dichloromethane/ethanol) and then on a column of silica (3/2 (v/v) diisopropyl ether/ethyl acetate) to give the derivative 33 (54.6 mg, 58%).

$[α]_D$ +55 (c=1, dichloromethane).

PREPARATION 24

Methyl O-(6-O-Acetyl-2,3,4-tri-O-methyl-α-D-glucopyranosyl)-(1→4)-O-(5-C-ethyl-2,3-di-O-methyl-β-D-glucopyranosyluronic acid)-(1→4)-O-(3,6-di-O-acetyl-α-D-glucopyranosyl)-(1→4)-O-(2,6-anhydro-5-C-carboxy-3-O-methyl-β-D-mannopyranosyl)-(1→4)-α-D-glucopyranoside (34).

A solution of compound 33 (40 mg, 0.024 mmol) in acetic acid (2 ml) is stirred under a hydrogen atmosphere in the presence of 10% palladium on charcoal (80 mg) for 16 hours, and filtered. The filtrate is concentrated to give compound 34.

PREPARATION 25

Methyl O-(2,3,4-tri-O-Methyl- α-D-glucopyranosyl)-(1→4)-O-(5-C-ethyl-2,3-di-O-methyl-β-D-glucopyranosyluronic acid)-(1→4)-O-(α-D-glucopyranosyl)-(1→)-O-(2,6-anhydro-5-C-carboxy-3-O-methyl-β-D-mannopyranosyl)-(1→4)-α-D-glucopyranoside (35).

Aqueous 5M sodium hydroxide solution (216 μl) is added to a solution of the crude compound 34 in methanol (866 μl). After 25 hours, water is introduced and the reaction mixture is passed through a column of Sephadex® G-25 gel (2×38 cm) eluted with water. The eluate is concentrated, passed through a Dowex® 50 H⁺ column (2 ml) and freeze-dried. At this stage, $^1$H NMR is used to check that all the protecting groups have been removed.

EXAMPLE 1

Methyl O-(2,3,4-tri-O-Methyl-6-O-sulpho-α-D-glucopyranosyl)-(1→4)-O-(2,3-di-O-methyl-βD-glucopyranosyluronic acid)-(1→4)-O-(2,3,6-tri-O-sulpho-α-D-glucopyranosyl)-(1→4)-O-(2,6-anhydro-5-C-carboxy-3-O-methyl-[α-L-idopyranosyluronic acid]α-D-mannopyranosyl)-(1→4)-2,3,6-tri-O-sulpho-α-D-glucopyranoside Sodium Salt (21).

According to C. A. A. van Boeckel and M. Petitou, Angew. Chem. Int. Ed. Engl., 1993, 32, 1671–1690.

A solution of compound 20 (20 mg, 20.7 Amol) and of triethylamine/sulphur trioxide complex (164 mg, 0.90 μmol) in dimethylformamide (2 ml) is heated at 55° C., protected from light, for 18 hours 30 minutes. The reaction mixture is cooled to room temperature and then diluted with aqueous 0.2M NaCl solution. The solution is then placed at the top of a column of Sephadex® G25F (170 ml) eluted with aqueous 0.2M NaCl solution.

The fractions containing the pentasaccharide are concentrated and desalified using the same column eluted with water. After freeze-drying, compound 21 is obtained (30.5 mg, 85%).

$[α]_D$ +49° C. (c×0.63, H₂O) $^1$H NMR given in Table 2 below.

TABLE 2

| Compound | Unit | H-1 | H-2 | H-3 | H-4 | H-5 | H-6 | H-6' | $J_{1-2}$ (Hz) |
|---|---|---|---|---|---|---|---|---|---|
| 21 ($D_2O$) | D | 5.46 | 3.32 | 3.55 | 3.34 | 3.87 | 4.28 | 4.12 | 3.9 |
| | E | 4.66 | 3.26 | 3.53 | 3.89 | 3.73 | — | — | 7.9 |
| | F | 5.50 | 4.36 | 4.81 | 4.00 | 4.17 | 4.49 | 4.41 | 3.7 |
| | G | 5.49 | 4.41 | 3.73 | 4.17 | — | 4.24 | 4.09 | ~1 |
| | H | 5.16 | 4.36 | 4.52 | 4.01 | 4.08 | 4.41 | 4.30 | 3.7 |

EXAMPLE 2

Methyl O-(2,3,4-tri-O-Methyl-6-O-sulpho-α-D-glucopyranosyl)-(1→4)-O-(5-C-ethyl-2,3-di-O-methyl-β-D-glucopyranosyluronic acid)-(1→4)-O-(2,3,6-tri-O-sulpho-α-D-glucopyranosyl)-(1→4)-O-(2,6-anhydro-5-C-carboxy-3-O-methyl-β-D-mannopyranosyl)-(1→4)-2,3,6-tri-O-sulpho-α-D-glucopyranoside, Sodium Salt (36).

Triethylamine/sulphur trioxide complex (91 mg) is added to a solution of the crude compound 35 in dimethylformamide (1.3 ml). After 20 hours at 55° C., the solution is placed at the top of a column of Sephadex® G-25 (2×38 cm) eluted with 0.2M sodium chloride. The fractions containing the product are concentrated and desalified using the same column eluted with water. Compound 36 is obtained after freeze-drying (21.9 mg, 52% from compound 33). $^1$H NMR given in Table 3 below.

Working as in Examples 1 and 2 above, compounds 37 to 40 of Examples 3 to 6 below are prepared. The $^1$H NMR spectra obtained for these compounds are in agreement with the configurations indicated below.

EXAMPLE 3

Methyl O-(2,3,4-tri-O-Methyl-6O-sulpho-α-D-glucopyranosyl)-(1→)-O-(2,3-di-O-methyl-)β-D-glucopyranosyl-uronic acid)-(1→4)-O-(2,3,6-tri-O-sulpho-α-D-glucopyranosyl)-(1→4)-O-(2,6-anhydro-5-C-carboxy-3O-methyl-β-D-mannopyranosyl)-(1→4)-2-O-sulpho-3,6-di-O-methyl-α-D-glucopyranoside, Sodium Salt (37).

[α]$_D$ +51° C. (c=0.48, water)

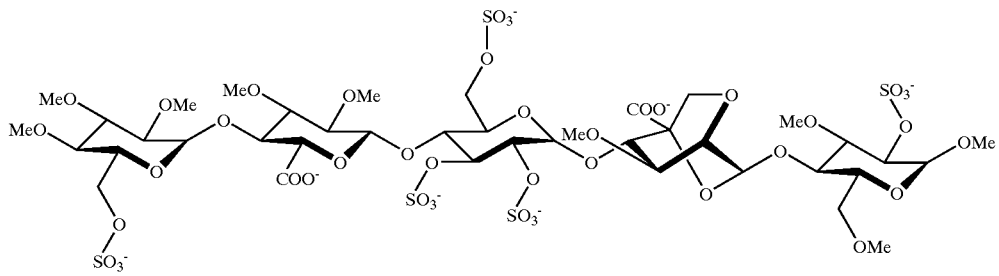

TABLE 3

| | H-1 ($J_{1-2}$ Hz) | H-2 | H-3 | H-4 | H-5 | H-6 | H-6' | Others |
|---|---|---|---|---|---|---|---|---|
| D | 5.43 (3.9) | 3.28 | 3.53 | 3.30 | 4.02 | 4.27 | 4.14 | |
| E | 4.68 (8.1) | 3.27 | 3.60 | 3.98 | — | — | — | 2.041/1.80: $CH_2CH_3$ 09.4: $CH_2CH_3$ |
| F | 5.50 (3.7) | 4.35 | 4.50 | 3.84 | 4.07 | 4.61 | 4.30 | |
| G | 5.47 (1.1) | 4.39 | 3.72 | 4.16 | — | 4.23 | 4.08 | |
| H | 5.16 (3.7) | 4.36 | 4.81 | 4.00 | 4.17 | 4.50 | 4.39 | |

EXAMPLE 4

Methyl O-(2,3,4-tri-O-Methyl-6-O-sulpho-α-D-gluco-pyranosyl)-(1→4)-O-(2,3-di-O-methyl-α-D-glucopyranosyl-uronic Acid)-(1→4)-O-(2,3,6-tri-O-sulpho-α-D-glucopyranosyl)-(1→4)-O-(2,6-anhydro-5-C-carboxy-3-O-methyl-β-D-mannopyranosyl)-(1→4)-2,3-di-O-sulpho-6-O-methyl-α-D-glucopyranoside, Sodium Salt (38).

[α]$_D$ +57° C. (c 0.28, water)

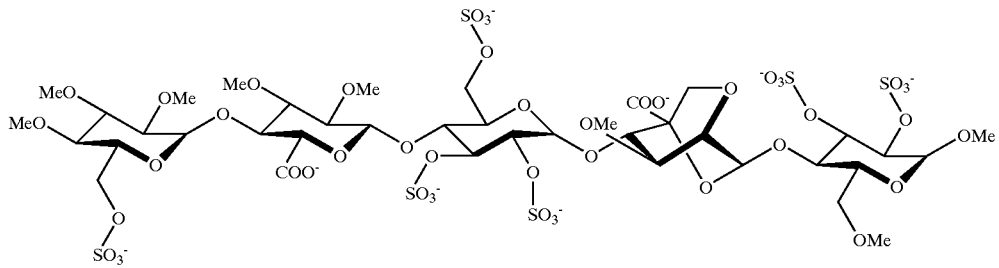

EXAMPLE 5

Methyl O-(2,3,4-tri-O-Methyl-6-O-sulpho-α-D-glucopyranosyl)-(1→4)-O-(2,3-di-O-methyl-β-D-glucopyranosyluronic acid)-(1→4)-O-(2,3,6-tri-O-sulpho-α-D-glucopyranosyl)-(1→4)-O-(2,6-anhydro-5-C-carboxy-3-O-methyl-β-D-mannopyranosyl)-(1→4)-2,6-di-O-sulpho-3-O-methyl-α-D-glucopyranoside, Sodium Salt (39).

$[\alpha]_D$ +53° C. (c=0.3, water)

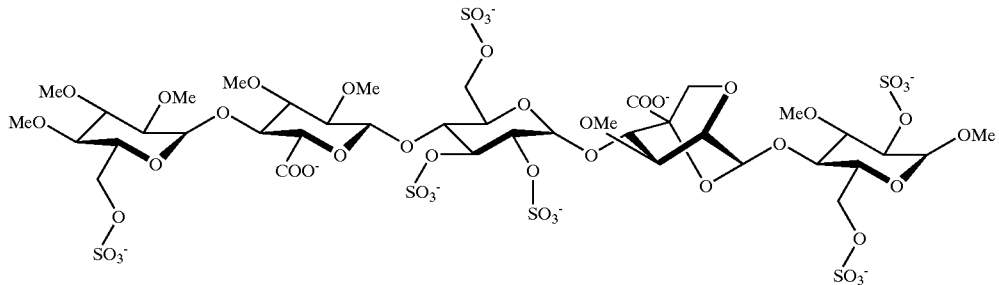

EXAMPLE 6

Methyl O-(2,3,4-tri-O-Methyl-6-O-sulpho-α-D-glucopyranosyl)-(1→4)-O-(2,3-di-O-methyl-β-D-glucopyranosyl-uronic Acid)-(1→4)-O-(2,3,6-tri-O-sulpho-α-d-glucopyranosyl)-(1→4)-O-(2,7-anhydro-5-C-carboxy-6-deoxy-3-O-methyl-β-d-mannoheptopyranosyl)-(1→4)-2,3,6-tri-O-sulpho-α-d-glucopyranoside, Sodium Salt (40).

$[\alpha]_D$ 49° C. (c=0.25, water)

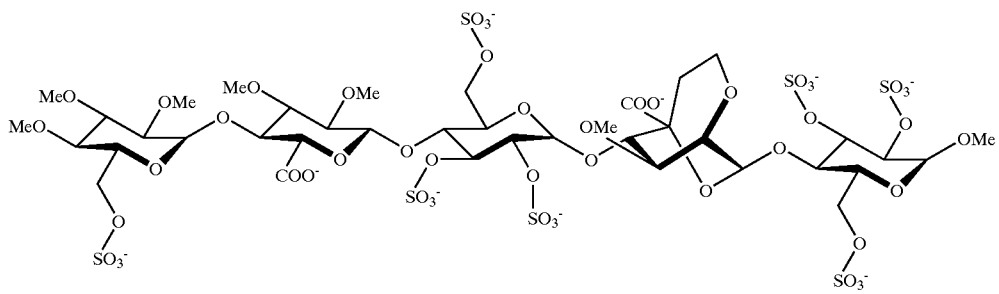

What is claimed is:

1. A pentasaccharide in acidic form and its pharmaceutically acceptable salts, the anionic form of which has the formula:

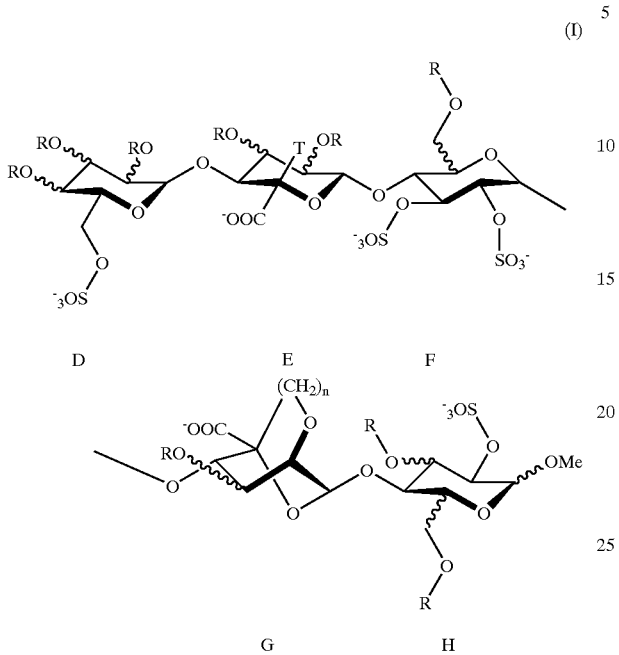

in which:
R represents hydrogen or an —$SO_3^-$, ($C_1$–$C_3$)alkyl or ($C_2$–$C_3$)acyl group;
T represents hydrogen or an ethyl group; and
n represents 1 or 2.

2. A pentasaccharide according to claim 1, in the form of the sodium salt or the potassium salt.

3. A pentasaccharide according to claim 2 selected from the group consisting of:
Methyl O-(2,3,4-tri-O-methyl-6-O-sulpho-α-D-glucopyranosyl)-(1→4)-O-(2,3-di-O-methyl-β-D-glucopyranosyluronic acid)-(1→4)-O-(2,3,6-tri-O-sulpho-α-D-glucopyranosyl)-(1→4)-O-(2,6-anhydro-5-C-carboxy-3-O-methyl-β-D-mannopyranosyl(1→4)-2,3,6-tri-O-sulpho-α-D-glucopyranoside, sodium salt;

Methyl O-(2,3,4-tri-O-methyl-6-O-sulpho-α-D-glucopyranosyl)-(1→4)-O-(5-C-ethyl-2,3-di-O-methyl-β-D-glucopyranosyluronic acid)-(1→4)-O-(2,3,6-tri-O-sulpho-α-D-glucopyranosyl)-(1→4)-O-(2,6-anhydro-5-C-carboxy-3-O-methyl-β-D-mannopyranosyl)-(1→4)-2,3,6-tri-O-sulpho-α-D-glucopyranoside, sodium salt;

Methyl O-(2,3,4-tri-O-methyl-6-O-sulpho-α-D-glucopyranosyl)-(1→4)-O-(2,3-di-O-methyl-β-D-glucopyranosyluronic acid)-(1→4)-O-(2,3,6-tri-O-sulpho-α-D-glucopyranosyl)-(1→4)-O-(2,6-anhydro-5-C-carboxy-3-O-methyl-β-D-mannopyranosyl)-(1→4)-2-O-sulpho-3,6-di-O-methyl-α-D-glucopyranoside, sodium salt;

Methyl O-(2,3,4-tri-O-methyl-6-O-sulpho-α-D-glucopyranosyl)-(1→4)-O-(2,3-di-O-methyl-β-D-glucopyranosyluronic acid)-(1→4)-O-(2,3,6-tri-O-sulpho-α-D-glucopyranosyl)-(1→4)-O-(2,6-anhydro-5-C-carboxy-3-O-methyl-β-D-mannopyranosyl)-(1→4)-2,3-di-O-sulpho-6-O-methyl-α-D-glucopyranoside, sodium salt;

Methyl O-(2,3,4-tri-O-methyl-6-O-sulpho-α-D-glucopyranosyl)-(1→4)-O-(2,3-di-O-methyl-β-D-glucopyranosyluronic acid)-(1→4)-O-(2,3,6-tri-O-sulpho-α-D-glucopyranosyl)-(1→4)-O-(2,6-anhydro-5-C-carboxy-3-O-methyl-β-D-mannopyranosyl)-(1→4)-2,6-di-O-sulpho-3-O-methyl-α-D-glucopyranoside, sodium salt; and Methyl O-(2,3,4-tri-O-methyl-6-O-sulpho-α-D-glucopyranosyl)-(1→4)-O-(2,3-di-O-methyl-β-D-glucopyranosyluronic acid)-(1→4)-O-(2,3,6-tri-O-sulpho-α-D-glucopyranosyl)-(1→4)-O-(2,7-anhydro-5-C-carboxy-6-deoxy-3-O-methyl-β-D-mannoheptopyranosyl)-(1→4)-2,3,6-tri-O-sulpho-α-D-glucopyranoside, sodium salt.

4. A pharmaceutical composition containing, as active principle, a pentasaccharide according to claim 1, in the form of a salt with a pharmaceutically acceptable base or in acidic form, combined with or mixed with a pharmaceutically acceptable, non-toxic inert excipient.

5. A pharmaceutical composition according to claim 4, in the form of a dosage unit containing from about 0.1 to about 100 mg of active principle.

6. A pharmaceutical composition according to claim 5, in which each dosage unit contains from about 0.5 to about 50 mg of active principle.

7. A pharmaceutical composition according to claim 4 wherein the pentasaccharide is in the form of a sodium or potassium salt.

8. A pharmaceutical composition containing, as active principle, a pentasaccharide according to claim 3.

9. A pharmaceutical composition according to claim 7 in the form of a dosage unit containing from about 0.1 to about 100 mg of active principle.

10. A pharmaceutical composition according to claim 8 in the form of a dosage unit containing form about 0.1 to about 100 mg of active principle.

11. A pharmaceutical composition according to claim 9 in which each dosage unit contains from about 0.5 to about 50 mg of active principle.

12. A pharmaceutical composition according to claim 10 in which each dosage unit contains from about 0.5 to about 50 mg of active principle.

13. A method for the treatment of pathologies associated with a clotting dysfunction which comprises administering to a patient in need of such treatment a polysaccharide according to claim 1.

14. A method according to claim 13 wherein the polysaccharide is in the form of a sodium or potassium salt.

15. A method for the treatment of pathologies associated with a clotting dysfunction which comprises administering to a patient in need of such treatment a polysaccharide according to claim 3.

* * * * *